(12) United States Patent
Liu et al.

(10) Patent No.: US 9,447,130 B1
(45) Date of Patent: Sep. 20, 2016

(54) PROCESS FOR THE PREPARATION OF DICYCLOPLATIN (71) Applicants: Syn-Nat Products Enterprise LLC, Edison, NJ (US); Medoc Pharmaceutical Co., Ltd, Changsha (CN)

(72) Inventors: Xiaozhong Liu, Potomac, MD (US); Jirui Xi, North Brunswick, NJ (US); Ye Zhao, North Brunswick, NJ (US); Liang Zhang, North Brunswick, NJ (US)

(73) Assignees: Syn-Nat Product Enterprise LLC, Edison, NJ (US); Medoc Pharmaceutical Co., Ltd., Changsha, Hunan (CN)

( * ) Notice: Subject to any disclaimer, the term of this patent is extended or adjusted under 35 U.S.C. 154(b) by 0 days.

(21) Appl. No.: 15/097,071

(22) Filed: Apr. 12, 2016

Related U.S. Application Data

(63) Continuation of application No. PCT/US2015/025334, filed on Apr. 10, 2015.

(51) Int. Cl.
*C07F 15/00* (2006.01)

(52) U.S. Cl.
CPC ....... *C07F 15/0093* (2013.01); *C07B 2200/13* (2013.01)

(58) Field of Classification Search
CPC .................................................. C07F 15/0093
USPC .......................................................... 556/137
See application file for complete search history.

(56) References Cited

U.S. PATENT DOCUMENTS 6,699,901 B1 3/2004 Yang
2009/0082438 A1 3/2009 Kataoka

FOREIGN PATENT DOCUMENTS

KR 20087021276 10/2008

OTHER PUBLICATIONS

International Search Report issued in corresponding International Patent Application No. PCT/US2015/025334 dated Jul. 1, 2015.

*Primary Examiner* — Porfirio Nazario Gonzalez
(74) *Attorney, Agent, or Firm* — Morgan Lewis & Bockius LLP (57) ABSTRACT

The present invention relates to a process to prepare dicycloplatin under mild reactive conditions and at fast reaction rates. The process is reproducible and easy to scale up for industrial application.

20 Claims, 4 Drawing Sheets

PROCESS FOR THE PREPARATION OF DICYCLOPLATIN

FIELD OF THE INVENTION

This invention relates to a new process for preparing an antitumor derivative of a double dicarboxylic acid diaminoplatin complex, named as dicycloplatin.

BACKGROUND OF THE INVENTION

Cisplatin has been used widely in clinical medicine as an antitumor drug since an antitumor effect was discovered for cis-dichlorodiaminoplatin. Rosenberg et al. *Nature,* 1965, 205: 698; *Nature,* 1972, 222: 385. Although a drug of this type exhibits therapeutic effects in cancers such as genitourinary cancer, nasopharyngeal cancer, cephalocircular cancer and lung cancer, it is toxic and leads to severe side effects. Some undesirable effects, such as nephrotoxicity, neurotoxicity, ototoxicity, nausea, and vomiting, are all constraints to its dosage and long term use. Carboplatin, one of the second-generation antitumor drugs of platin analogues, has an antitumor spectrum similar to that of cisplatin and is susceptible to cross drug-resistance. The therapeutic effect of carboplatin is slightly inferior to that of cisplatin. Although the toxicity and associated side effects of carboplatin is significantly less than that of cisplatin, myelosuppression still exists, and cisplatin is not stable as an aqueous solution. As a result, active studies in search of highly potent antitumor drugs from platin analogues with low toxicity and broad-spectrum effects have continued.

Dicycloplatin (DCP) is a super molecule composed of carboplatin (CBP) and 1,1-cyclobutane dicarboxylate (CB-DCA) joined together by hydrogen bonds. The solubility and stability of platinum complexes have a direct bearing on their activity, toxicity and pharmacokinetics. Preclinical studies have shown that DCP overcomes the problem of CBP instability in aqueous solution while maintaining CBP's anticancer effects. Clinical evaluation in a Phase I dose-escalation study in patients with tumors showed that DCP was tolerated at doses ranging from 100 to 550 mg/m$^2$ and showed potential efficacy in Chinese cancer patients. DCP showed favorable bioavailability and stability in vivo, with the recommended Phase II dosage for DCP-containing chemotherapy being 450 mg/m$^2$. DCP is currently being investigated as a monotherapy in several cancer types, such as prostatic carcinoma, and in combination with paclitaxel in a Phase II non-lung cancer study. The chemical structure of DCP is shown as formula I:

(I)

Dicycloplatin (DCP) was first reported in U.S. Pat. No. 6,699,901, which disclosed the chemical structure and process for preparation of DCP.

The crystal structure of DCP has been determined and reported in "Structural studies of dicycloplatin-an antitumor supramolecule." Yang X. et al., *Science China Chemistry,* 40(5): 485-491 (2010), which shows dicycloplatin as a co-crystal composed of carboplatin and 1,1-cyclobutane dicarboxylate.

However, the processes disclosed in U.S. Pat. No. 6,699,901, which were tested by the inventors of the present invention, cannot produce satisfying results and are difficult to scale up for industrial-scale production. The preparation of dicycloplatin according to the method of U.S. Pat. No. 6,699,901 produced a mixture of carboplatin and dicycloplatin, resulting in high toxicity and unacceptable products.

Therefore, it is desirable to provide robust and easy-to-scale-up crystallization processes to efficiently obtain pure dicycloplatin in high yield.

SUMMARY OF THE INVENTION

The present invention provides a surprisingly discovered new process for preparing dicycloplatin with the benefits of easy operation, mild reactive conditions, short reaction times and high reproducibility.

Accordingly, the present invention provides a process for preparing dicycloplatin, comprising: suspending per unit carboplatin in a corresponding proportion of 1, 1-cyclobutane dicarboxylic acid and solvent(s); followed by crystallizing or precipitating the dicycloplatin through stirring, evaporating the solvent(s), and/or cooling.

An aspect of the invention is a process for preparing dicycloplatin of formula (I), (I)

comprising: combining carboplatin with a corresponding proportion of 1,1-cyclobutane dicarboxylic acid and a solvent to form a suspension; separating formed precipitated solids from the suspension; and drying the solids, wherein the solids comprise the dicycloplatin of formula (I) without any amount of carboplatin detectable by XRPD.

In an embodiment, the process further comprises cooling the precipitating solids before the separating step.

In an embodiment, the process further comprises agitating the suspension after the combining step and before the separating step.

In an embodiment, the solids consist essentially of dicycloplatin.

In an embodiment, the solids consist of dicycloplatin.

In an embodiment, the solvent used in the process is water.

In an embodiment, the molar ratio of the carboplatin and the 1,1-cyclobutane dicarboxylic acid in the combining step ranges from about 1:15 to about 1:50.

In an embodiment, the molar ratio of the carboplatin and the 1,1-cyclobutane dicarboxylic acid in the combining step ranges from about 1:1.15 to about 1:2.

In an embodiment, the molar ratio of the carboplatin and the 1,1-cyclobutane dicarboxylic acid in the combining step ranges from 1:3 to about 1:50.

In an embodiment, the molar ratio of the carboplatin and the 1,1-cyclobutane dicarboxylic acid in the combining step ranges from 1:5 to 1:10.

In an embodiment, the proportion of the weight of carboplatin in grams and the volume of the solvent in mL in the combining step ranges from about 1:2 to about 1:50.

In an embodiment, the proportion of the weight of the carboplatin in grams and the volume of the solvent in mL in the combining step ranges from about 1:3 to about 1:5.

Figure 2:
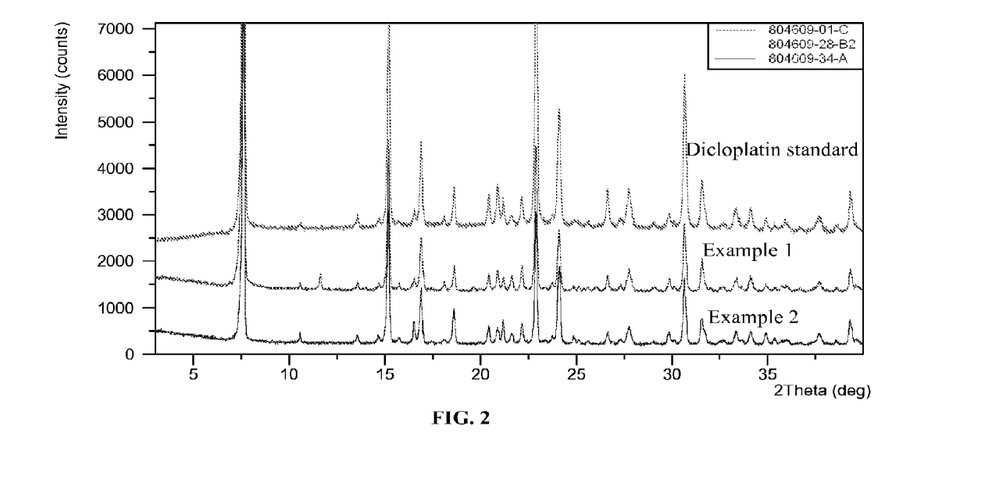
FIG. 2 shows a representative X-ray powder diffraction (XRPD) pattern of the product, where the product contains dicycloplatin (bottom pattern) and is compared to a standard XRPD pattern of dicycloplatin (top pattern).

In an embodiment, the dicycloplatin has an X-ray powder diffraction pattern substantially as depicted in FIG. 2.

In an embodiment, the reaction temperature of the combining step ranges from 0° C. to 80° C.

In an embodiment, the reaction temperature of the combining step ranges from 10 to 25° C.

In an embodiment, the solvent is an organic solvent selected from the group consisting of: tetrahydrofuran (THF), dichloromethane (DCM), isopropanol, ethanol, ethyl acetate (EtOAc), dimethylformamide (DMF), 1,4-dixoane, acetone, toluene, isobutyl acetate, isopropyl acetate, chloroform, 2-methoxyethanol, methyl isobutyl ketone (MIBK), methyl tert-butyl ether (MTBE), 1,2-dichloro ethane and a mixture thereof.

In an embodiment, the solvent is a mixture of water and an organic solvent selected from the group consisting of: THF, DCM, isopropanol, ethanol, EtOAc, DMF, 1,4-dixoane, acetone, toluene, isobutyl acetate, isopropyl acetate, chloroform, 2-methoxyethanol, MIBK, MTBE, 1,2-dichloro ethane and a mixture thereof.

In an embodiment, the reaction temperature of the combining step ranges from 0° C. to 80° C.

In an embodiment, the reaction temperature of the combining step ranges from 20 to 35° C.

In some embodiments, the final product does not contain carboplatin in an amount detectable with X-ray Powder Diffraction (XRPD).

In some embodiments, the final product does not contain carboplatin in an amount detectable with Differential Scanning calorimetry (DSC).

In some embodiments, the final product does not contain carboplatin in an amount detectable with either XRPD or DSC.

BRIEF DESCRIPTION OF THE DRAWINGS

The following figures find a basis in Examples 7-9 as described herein and are employed as merely illustrative of particular embodiments of the present invention, and with no intention of limiting the scope of the invention.

DETAILED DESCRIPTION OF THE INVENTION

The following description of certain embodiment(s) is merely exemplary in nature and is in no way intended to limit the invention, its application, or uses. As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The present invention provides a new process for preparing dicycloplatin this is easy to operate, involves mild reactive conditions and has a short reaction time. The new process is reproducible and readily scaled up for industrial application. In some embodiments, only water is used as a solvent (i.e., no organic solvent). In some embodiments, only one organic solvent or a mixture of organic solvents is used. In some embodiments, a mixture of organic solvent and water is used.

In an exemplary embodiment, the present invention provides a process for producing dicycloplatin, comprising: suspending carboplatin in corresponding proportion of 1,1-cyclobutane dicarboxylic acid and a solvent to form a suspension; stirring the suspension to form precipitating solids; and drying the solids, wherein the solids comprise dicycloplatin of formula I and does not contain carboplatin.

In some embodiments, the process further comprises cooling the precipitating solids. In some embodiments, the process further comprises filtering the precipitating solids. In some embodiments, the process further comprises re-crystallizing the solids.

In some embodiments, the solvent is water.

In some embodiments, the molar ratio of carboplatin and 1,1-cyclobutane dicarboxylic acid is lower than 1:1. In some embodiments, the molar ratio of carboplatin and 1,1-cyclobutane dicarboxylic acid is lower than 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:11, 1:12, 1:13, 1:14, 1:15, 1:20, 1:25, 1:30, 1:35, 1:40, 1:45, or 1:50.

In some specific embodiments, the molar ratio of carboplatin and 1,1-cyclobutane dicarboxylic acid ranges from about 1:1.15 to about 1:2, from about 1:1.15 to about 1:3, from about 1:1.15 to about 1:4, from about 1:1.15 to about 1:5, from about 1:1.15 to about 1:6, from about 1:1.15 to about 1:7, from about 1:1.15 to about 1:8, from about 1:1.15 to about 1:9, from about 1:1.15 to about 1:10, from about 1:1.15 to about 1:15, from about 1:1.15 to about 1:20, from about 1:1.15 to about 1:25, from about 1:1.15 to about 1:30, from about 1:1.15 to about 1:40, from about 1:1.15 to about 1:50.

In some embodiments, the proportion of carboplatin (weight, g) and solvent (volume, mL) ranges from about 1:2 to about 1:50. In some specific embodiments, the proportion of carboplatin (weight, g) and solvent (volume, mL) ranges from about 1:3 to about 1:5.

In some embodiments, the final dicycloplatin product does not contain carboplatin in an amount of more than 5%, 3%, 1%, 0.5%, 0.1%, 0.05%, 0.01%, 0.005%, or 0.001% of the final product by weight.

In some embodiments, the final dicycloplatin product is at least 95%, 96%, 97%, 98%, 99% or 99.9% pure.

The reactions are typically carried out under mild temperature. However, the reactions can also be processed under high temperatures or low temperatures. The reactions are typically carried out under normal pressure. However, the reactions can also be processed under increased pressure or decreased pressure.

In some embodiments, organic solvents may be used as the solvent to produce the desired products. Exemplary organic solvents include, but are not limited to, THF, DCM, isopropanol, ethanol, EtOAc, DMF, 1,4-dixoane, acetone, toluene, isobutyl acetate, isopropyl acetate, chloroform, 2-methoxyethanol, MIBK, MTBE, 1,2-dichloro ethane and mixtures of two or more solvents, or mixtures of water and organic solvents. In some specific embodiments, the organic solvent is DCM.

The following non-limiting examples further illustrate certain aspects of the present invention.

EXAMPLES

X-Ray Powder Diffraction (XRPD)

Analytical Instrument: Panalytical Empyrean. The X-ray powder diffraction was conducted by mounting a sample of the crystalline material on a Si single crystal low-background holder and spreading out the sample into a thin layer with the aid of a microscope slide. The 2-theta (2-θ) position was calibrated against a Panalytical 640 Si powder standard. The sample was irradiated with X-rays generated by a copper long-fine focus tube operated at 45 kV and 40 mA with a wavelength of Kα1=1.540589 angstroms and Kα2=1.544426 angstroms (Kα2/Kα1 intensity ratio is 0.50). The collimated X-ray source was passed through a programmed divergence slit set at 10 mm and the reflected radiation directed through a 5.5 mm anti-scatter slit. The sample was exposed for 16.3 seconds per 0.013° 2-theta increment (continuous scan mode) over the range of 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software.

It is known in the art that the relative intensities of peaks can be affected by, for example, grains above 30 microns in size and that non-unitary aspect ratios may affect analysis of samples. It is also known that the position of reflections can be affected by the precise height at which the sample sits in the diffractometer and the zero calibration of the diffractometer. The surface planarity of the sample may also have a limited effect. As a result, the diffraction pattern data presented are not intended to be limited to the absolute values.

Differential Scanning Calorimetry (DSC)

DSC was used as a thermoanalytical method to measure the difference in the amount of heat required to increase the temperature of a sample and reference was measured as a function of temperature. The general process of DSC is known and the specific instruments and conditions employed in the described Examples were as follows:
Analytical Instrument: TA Instruments Q2000 DSC;
Heating rate: 10° C. per minute; and
Purge gas: nitrogen.

Thermal Gravimetric Analysis (TGA)

TGA was used to measure changes in physical and chemical properties of samples as a function of increasing temperature (with a constant heating rate), or as a function of time (with constant temperature and/or constant mass loss). The general process of TGA is known and the specific instruments and conditions in the described Examples were as follows:
Analytical Instrument: TA Instruments Q5000 TGA;
Heating rate: 10° C. per minute; and
Purge gas: nitrogen.

$^1$H Nuclear Magnetic Resonance ($^1$H NMR)

The general process of $^1$H NMR spectroscopy is known and the specific instruments and conditions employed in the described Examples were as follows: solution NMR was collected on a Bruker 400M NMR Spectrometer using DMSO-d6.

Example 1

Preparation Procedures for Dicycloplatin

1) Charged 5.0 g of carboplatin (13.47 mmol) and 2.232 g of 1,1-cyclobutane dicarboxylic acid (15.50 mmol) into a 20-mL glass vial.
2) Added 12.5 mL of deionized water into the same vial and stirred the mixture at RT (room temperature) to form uniform suspension while keeping the vial away from light.
3) Cooled the mixture to 5° C. at a rate of 0.33° C./min and aged at 5° C. for 20 hours to form a precipitation cake.
4) Vacuum filtered and washed the cake with 5 mL of deionized water, and then vacuum dried the wet cake.
5) Collected the solids from the dried cake and measured the amount of dicycloplatin.
6) 6.49 g dicycloplatin was obtained with an overall yield of 93.2%.

The product was analyzed by XRPD, DSC, TGA and $^1$H NMR.

$^1$H NMR results: (400 MHz, DMSO-d6) δ 12.63 (s, 2H), 4.09 (s, 6H), 2.67 (t, J=7.9 Hz, 4H), 2.37 (t, J=8.0 Hz, 4H), 1.95-1.76 (m, 2H), 1.73-1.55 (m, 2H).

The XRPD data are listed in Table 1.

TABLE 1

| 2-theta | d-spacing | intensity % |
|---|---|---|
| 7.5 | 11.8 | 100.0 |
| 15.0 | 5.9 | 46.7 |
| 16.4 | 5.4 | 6.0 |
| 16.8 | 5.3 | 12.7 |
| 18.5 | 4.8 | 9.8 |
| 20.8 | 4.3 | 8.6 |
| 21.1 | 4.2 | 5.1 |
| 21.5 | 4.1 | 7.7 |
| 22.0 | 4.0 | 10.7 |
| 22.8 | 3.9 | 15.6 |
| 24.0 | 3.7 | 16.6 |
| 26.5 | 3.4 | 5.4 |
| 29.7 | 3.0 | 5.5 |
| 30.5 | 2.9 | 6.5 |
| 33.2 | 2.7 | 4.6 |

Example 2

Preparation Procedures for Dicycloplatin

1) Charged 1.0 g of carboplatin (2.69 mmol) and 776.4 mg of 1,1-cyclobutane dicarboxylic acid (5.39 mmol) into a 20-mL glass vial.

2) Added 5 mL of deionized water into the same vial and stirred the suspension at RT for 6 hours while keeping the vial away from light to form a precipitation cake.
3) Vacuum filtered and washed the cake with 2.8 mL of deionized water rapidly, and then vacuum dried the wet cake.
4) Collected the solids from the dried cake and measured the amount of dicycloplatin.

The product was analyzed by XRPD, DSC, TGA and $^1$H NMR.

$^1$H NMR results: (400 MHz, DMSO-d6) δ 12.65 (s, 2H), 4.09 (s, 6H), 2.67 (t, J=7.9 Hz, 4H), 2.37 (t, J=8.0 Hz, 4H), 1.92-1.77 (m, 2H), 1.72-1.57 (m, 2H).

The XRPD data are listed in Table 2.

TABLE 2

| 2-theta | d-spacing | intensity % |
| --- | --- | --- |
| 7.6 | 11.7 | 100.0 |
| 15.1 | 5.9 | 66.3 |
| 16.5 | 5.4 | 11.8 |
| 16.8 | 5.3 | 23.6 |
| 18.5 | 4.8 | 17.1 |
| 20.8 | 4.3 | 15.3 |
| 21.5 | 4.1 | 12.1 |
| 22.1 | 4.0 | 17.8 |
| 22.8 | 3.9 | 33.8 |
| 24.0 | 3.7 | 34.2 |
| 26.5 | 3.4 | 12.3 |
| 29.8 | 3.0 | 11.6 |
| 30.6 | 2.9 | 18.6 |
| 31.5 | 2.8 | 11.7 |
| 33.3 | 2.7 | 11.8 |

Example 3

Preparation procedures for dicycloplatin

1) Charged 5.0 g of carboplatin (13.47 mmol) and 2.523 g of 1,1-cyclobutane dicarboxylic acid (17.52 mmol) into a 100-mL glass vial.
2) Added 25 mL of deionized water into the same vial and stirred the suspension at RT for 5 hours while keeping the vial away from light to form a precipitation cake.
3) Vacuum filtered and washed the cake with 5 mL of deionized water rapidly, and then vacuum dried the wet cake.
4) Collected the solids from the dried cake and measured the amount of dicycloplatin.
5) 5.88 g of dicycloplatin was obtained with an overall yield of 84.2%.

The product was analyzed by XRPD, DSC, TGA and $^1$H NMR.

$^1$H NMR results: (400 MHz, DMSO-d6) δ 12.63 (s, 2H), 4.09 (s, 6H), 2.67 (t, J=7.9 Hz, 4H), 2.37 (t, J=8.0 Hz, 4H), 1.90-1.80 (m, 2H), 1.70-1.59 (m, 2H).

The XRPD data are listed in Table 3.

TABLE 3

| 2-theta | d-spacing | intensity % |
| --- | --- | --- |
| 7.5 | 11.8 | 100.0 |
| 15.0 | 5.9 | 90.9 |
| 16.4 | 5.4 | 13.8 |
| 16.8 | 5.3 | 24.2 |
| 18.5 | 4.8 | 22.9 |
| 21.1 | 4.2 | 10.8 |
| 22.0 | 4.0 | 11.4 |
| 22.8 | 3.9 | 30.9 |
| 24.0 | 3.7 | 37.4 |
| 26.5 | 3.4 | 6.5 |
| 29.7 | 3.0 | 8.8 |
| 30.5 | 2.9 | 16.9 |
| 31.4 | 2.8 | 8.4 |
| 31.6 | 2.8 | 8.0 |
| 33.2 | 2.7 | 10.6 |

Example 4

Preparation Procedures for Dicycloplatin

1) Weighed 5.0 g of carboplatin (13.47 mmol) and 2.523 g of 1,1-cyclobutane dicarboxylic acid (17.52 mmol) into a 100-mL glass vial.
2) Added 25 mL of deionized water into the same vial and stirred the mixture at RT to form a uniform suspension while keeping the vial away from light.
3) Cooled the mixture to 5° C. at a rate of 0.33° C./min and aged at 5° C. for 19 hours to form a precipitation cake.
4) Vacuum filtered and dried the wet cake.
5) Collected the solids from the dried cake and measured the amount of dicycloplatin.
6) 6.11 g of dicycloplatin was obtained with an overall yield of 87.1%.

The product was analyzed by XRPD, DSC, TGA and $^1$H NMR.

$^1$H NMR results: (400 MHz, DMSO-d6) δ 12.65 (s, 2H), 4.09 (s, 6H), 2.67 (t, J=7.9 Hz, 4H), 2.37 (t, J=8.0 Hz, 4H), 1.94-1.77 (m, 2H), 1.74-1.51 (m, 2H).

The XRPD data are listed in Table 4.

TABLE 4

| 2-theta | d-spacing | intensity % |
| --- | --- | --- |
| 7.6 | 11.7 | 100.0 |
| 15.1 | 5.9 | 20.6 |
| 16.4 | 5.4 | 2.9 |
| 16.8 | 5.3 | 8.9 |
| 18.5 | 4.8 | 4.7 |
| 20.3 | 4.4 | 2.8 |
| 20.8 | 4.3 | 4.0 |
| 21.5 | 4.1 | 2.5 |
| 22.1 | 4.0 | 4.5 |
| 22.8 | 3.9 | 11.4 |
| 24.0 | 3.7 | 9.6 |
| 26.5 | 3.4 | 3.0 |
| 29.8 | 3.0 | 2.4 |
| 30.6 | 2.9 | 5.1 |
| 31.5 | 2.8 | 2.7 |

Example 5

Preparation Procedures for Dicycloplatin

1) Added 60.08 g of 1,1-cyclobutane dicarboxylic acid (417.22 mmol) and 593 mL of deionized water into a 1-L shaded crystallizer.
2) Charged 118.6 g of carboplatin (319.46 mmol) into the same crystallizer and stirred the mixture for 6 hours at RT.
3) Cooled the mixture to 5° C. at a rate of 0.33° C./min and aged at 5° C. for 19 hours to form a precipitation cake.
4) Vacuum filtered and washed the cake with 120 mL of deionized water, and then vacuum dried the wet cake.

5) Collected the solids from the dried cake and measured the amount of dicycloplatin.
6) 148.52 g of dicycloplatin was obtained with overall yield of 90.2%.

The product was analyzed by XRPD, DSC, TGA and $^1$H NMR.

$^1$H NMR results: (400 MHz, DMSO-d6) δ 12.63 (s, 2H), 4.09 (s, 6H), 2.67 (t, J=7.9 Hz, 4H), 2.37 (t, J=8.0 Hz, 4H), 1.95-1.77 (m, 2H), 1.73-1.55 (m, 2H).

The XRPD data are listed in Table 5.

TABLE 5

| 2-theta | d-spacing | intensity % |
| --- | --- | --- |
| 7.5 | 11.8 | 100.0 |
| 15.0 | 5.9 | 23.5 |
| 16.4 | 5.4 | 3.1 |
| 16.8 | 5.3 | 8.3 |
| 18.5 | 4.8 | 4.7 |
| 20.3 | 4.4 | 2.8 |
| 21.1 | 4.2 | 2.4 |
| 22.0 | 4.0 | 1.5 |
| 22.8 | 3.9 | 17.4 |
| 24.0 | 3.7 | 9.5 |
| 26.5 | 3.4 | 1.0 |
| 27.7 | 3.2 | 2.4 |
| 30.6 | 2.9 | 7.3 |
| 31.4 | 2.8 | 3.3 |
| 39.2 | 2.3 | 2.5 |

Example 6

Preparation Procedures for Dicycloplatin

1) Added 2.239 g of 1,1-cyclobutane dicarboxylic acid (15.55 mmol) and 15 mL of deionized water into a 20-mL glass vial.
2) Charged 5.0 g of carboplatin (13.47 mmol) into the same vial and stirred the mixture at RT.
3) Cooled the mixture to 5° C. at a rate of 0.33° C./min and aged at 5° C. for 19 hours to form a precipitation cake.
4) Vacuum filtered and washed the cake with 5 mL of deionized water, and then vacuum dried the wet cake.
5) Collected the solids and measured the amount of cycloplatin.
6) 6.40 g of dicycloplatin was obtained with overall yield of 92.2%.

The product was analyzed by XRPD, DSC, TGA and $^1$H NMR.

$^1$H NMR results: (400 MHz, DMSO-d6) δ 12.63 (s, 2H), 4.09 (s, 6H), 2.67 (t, J=7.9 Hz, 4H), 2.37 (t, J=8.0 Hz, 4H), 1.93-1.75 (m, 2H), 1.74-1.51 (m, 2H).

The XRPD data are listed in Table 6.

TABLE 6

| 2-theta | d-spacing | intensity % |
| --- | --- | --- |
| 7.6 | 11.7 | 100.0 |
| 15.2 | 5.8 | 30.9 |
| 16.5 | 5.4 | 3.7 |
| 16.9 | 5.2 | 9.8 |
| 18.6 | 4.8 | 5.9 |
| 20.4 | 4.3 | 3.6 |
| 20.9 | 4.3 | 5.5 |
| 22.1 | 4.0 | 5.6 |
| 22.9 | 3.9 | 21.0 |
| 24.1 | 3.7 | 12.4 |
| 26.6 | 3.3 | 3.0 |
| 27.8 | 3.2 | 3.4 |
| 30.7 | 2.9 | 8.7 |
| 31.6 | 2.8 | 4.5 |
| 39.3 | 2.3 | 3.6 |

Representative Results from Examples 1-6

Figure 1:
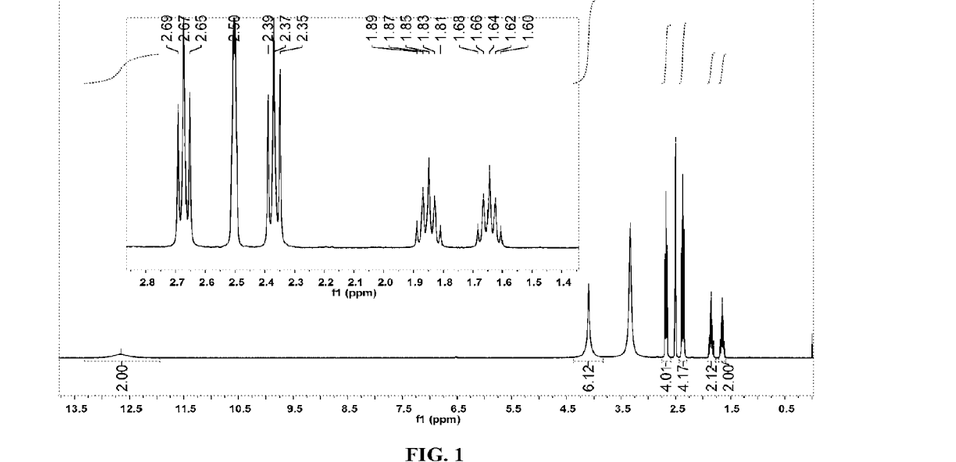
FIG. 1 shows a representative $^1$H-NMR spectrum of the product, where the product contains dicycloplatin and is dissolved in DMSO-$d_6$.

The $^1$H NMR spectra from Examples 1-6 are highly similar. FIG. 1 shows a representative $^1$H NMR spectrum of a product obtained in Example 1. The $^1$H NMR spectrum indicates the product contained dicycloplatin and that the molar ratio of the two components (1,1-cyclobutane dicarboxylic acid and carboplatin) in dicycloplatin is 1:1.

The X-ray powder diffraction (XRPD) patterns from Examples 1-6 are also highly similar. FIG. 2 shows the representative XRPD pattern of a product obtained in Examples 1 and 2 compared to a standard XRPD pattern of dicycloplatin (based on Yang et al., *Science China Chemistry*, 40(5): 485-491 (2010)), indicating that the sample was dicycloplatin.

Figure 3:
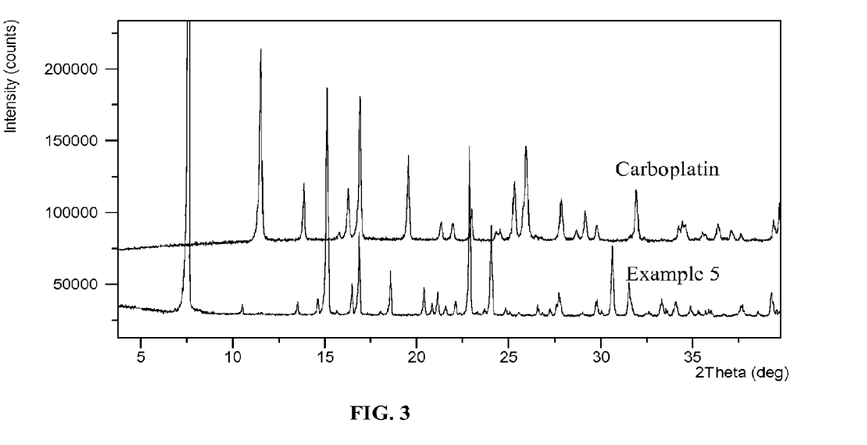
FIG. 3 shows a representative XRPD pattern of the product, where the product contains dicycloplatin (bottom pattern) and is compared to an XRPD pattern of carboplatin (top pattern).

FIG. 3 shows a representative XRPD pattern of a product obtained in Example 5 compared to a standard XRPD pattern of carboplatin, indicating that there was no traceable carboplatin in the sample obtained in the above Examples.

Figure 4:
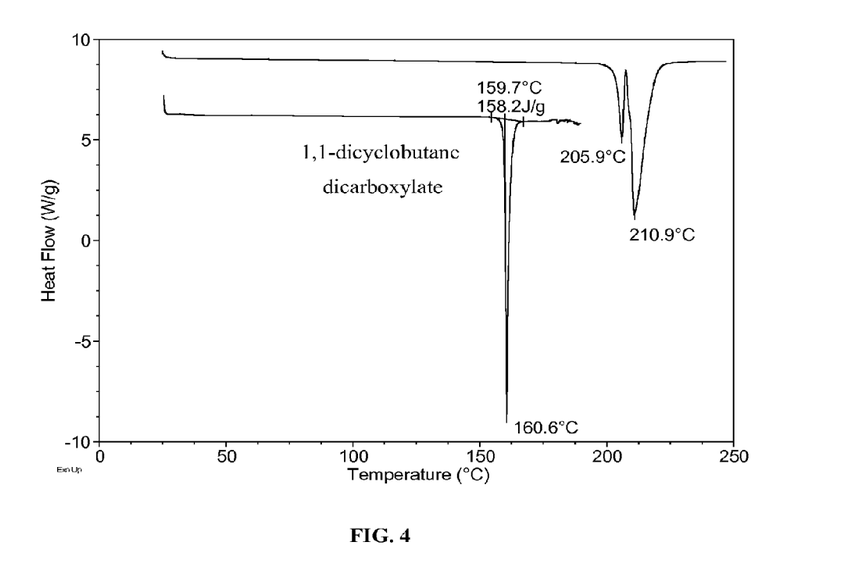
FIG. 4 shows a representative differential scanning calorimetric (DSC) thermogram of the product, where the product contains dicycloplatin (bottom pattern) and is compared to a DSC thermogram of 1,1-cyclobutane dicarboxylate (top pattern).

The differential scanning calorimetry (DSC) thermograms from the Examples 1-6 are also highly similar. FIG. 4 shows a representative DSC thermogram of dicycloplatin obtained in Example 5, showing that there was no evidence of 1,1-cyclobutane dicarboxylic acid (i.e., no signal of the melting point of 1,1-cyclobutane dicarboxylic at 159.7° C.) present in the products obtained in the above Examples.

Figure 5:
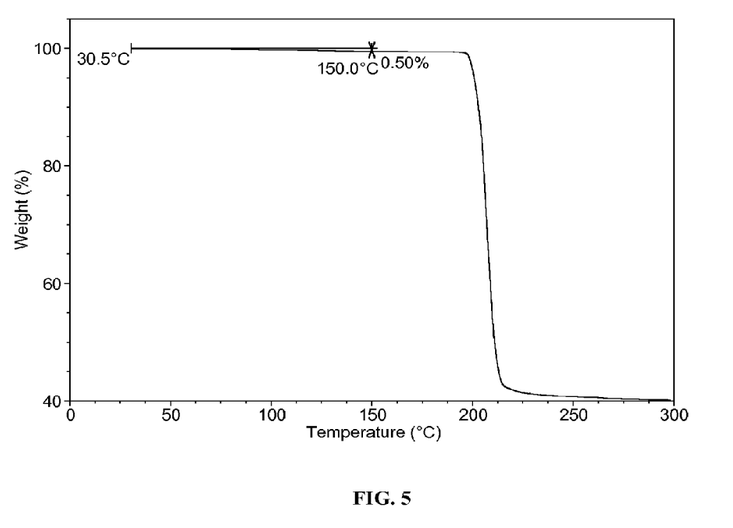
FIG. 5 shows a representative thermal gravimetric analysis (TGA) thermogram of the product, where the product contains dicycloplatin (bottom pattern).

The representative thermal gravimetric analysis (TGA) thermograms from Examples 1-6 are also highly similar. FIG. 5 shows a representative TGA thermogram of a product obtained in Example 5. The dicycloplatin has a TGA thermogram comprising about 0.5% weight loss up to 150° C.

Example 7

Preparation Procedures for Dicycloplatin

1) Dissolved 50.0 mg of carboplatin (135 μmol) in 2.8 mL of water in a 3-mL glass vial at RT.
2) Added 19.4 mg of 1,1-cyclobutane dicarboxylic acid (135 μmol) into the same vial.
3) Stirred the suspension at RT to obtain a clear solution.
4) Transferred the clear solution to a 25-mL round-bottom flask and rotary evaporated at a temperature between 50° C. and 55° C. to obtain white crystal solid.
5) Air-dried the solid to obtain a product.

The product was analyzed by XRPD, DSC and TGA.
The XRPD data are listed in Table 7.

TABLE 7

| 2-theta | d-spacing | intensity % |
| --- | --- | --- |
| 7.6 | 11.6 | 100.0 |
| 15.1 | 5.9 | 82.9 |
| 16.5 | 5.4 | 23.4 |
| 16.9 | 5.3 | 13.9 |
| 18.6 | 4.8 | 44.9 |
| 21.2 | 4.2 | 15.0 |
| 22.9 | 3.9 | 16.5 |
| 24.1 | 3.7 | 33.2 |

TABLE 7-continued

| 2-theta | d-spacing | intensity % |
|---|---|---|
| 24.1 | 3.7 | 15.8 |
| 24.8 | 3.6 | 7.8 |
| 30.6 | 2.9 | 10.3 |
| 31.7 | 2.8 | 11.9 |
| 33.3 | 2.7 | 11.7 |
| 33.4 | 2.7 | 6.2 |
| 37.6 | 2.4 | 9.2 |

Example 8

Preparation Procedures for Dicycloplatin

1) Dissolved 15.1 mg of carboplatin (41 μmol) and 5.9 mg of 1,1-cyclobutane dicarboxylic acid (41 μmol) in 1.0 mL of water in a 3-mL glass vial.
2) After filtering by 0.45 μm filter membrane, the filtrate was transferred to a 4-mL glass.

Covered the vial with aluminum-foil paper to keep solution away from light and evaporated the solution freely at RT.

The product was analyzed by XRPD, DSC and TGA. The XRPD data are listed in Table 8.

TABLE 8

| 2-theta | d-spacing | intensity % |
|---|---|---|
| 7.5 | 11.8 | 100.0 |
| 15.1 | 5.9 | 41.3 |
| 16.8 | 5.3 | 18.0 |
| 18.5 | 4.8 | 11.4 |
| 20.8 | 4.3 | 11.1 |
| 22.0 | 4.0 | 11.2 |
| 22.8 | 3.9 | 34.8 |
| 24.0 | 3.7 | 28.9 |
| 26.5 | 3.4 | 10.5 |
| 27.6 | 3.2 | 8.4 |
| 30.6 | 2.9 | 19.4 |
| 31.5 | 2.8 | 8.0 |

Example 9

Preparation Procedures for Dicycloplatin

1) Charged 49.7 mg of carboplatin (134 μmol) in 2.8 mL of water in a 3-mL of vial and stirred the suspension to obtain a clear solution at RT.
2) Added 19.4 mg of 1,1-cyclobutane dicarboxylic acid (135 μmol) into the same vial.
3) Stirred the solution in a vial wrapped with aluminum-foil at RT.
4) Solid was observed after slurry for about 15 min and isolated by centrifuging.

The product was analyzed by XRPD, DSC and TGA. The XRPD data are listed in Table 9.

TABLE 9

| 2-theta | d-spacing | intensity % |
|---|---|---|
| 7.6 | 11.6 | 23.4 |
| 14.7 | 6.0 | 6.1 |
| 15.0 | 5.9 | 14.2 |
| 15.2 | 5.8 | 100.0 |
| 15.4 | 5.8 | 4.6 |
| 16.5 | 5.4 | 9.0 |

TABLE 9-continued

| 2-theta | d-spacing | intensity % |
|---|---|---|
| 22.9 | 3.9 | 5.9 |
| 24.1 | 3.7 | 9.2 |
| 24.2 | 3.7 | 4.4 |
| 29.8 | 3.0 | 11.3 |
| 29.9 | 3.0 | 6.0 |
| 31.7 | 2.8 | 13.7 |
| 31.8 | 2.8 | 7.3 |
| 33.4 | 2.7 | 6.7 |
| 33.5 | 2.7 | 4.0 |

Test According to a Reported Process.

Examples 7-9 represent experiments conducted according to the reported process in U.S. Pat. No. 6,699,901. In brief, carboplatin was dissolved in water and cyclobutane dicarboxylic acid was added to the solution while stirring. The molar ratio of the carboplatin and the cyclobutane dicarboxylic acid was 1:1. The mixture was completely dissolved and the solution was evaporated to produce a dried product. The XRPD pattern results for the product are shown in FIG. 6.

Figure 6:
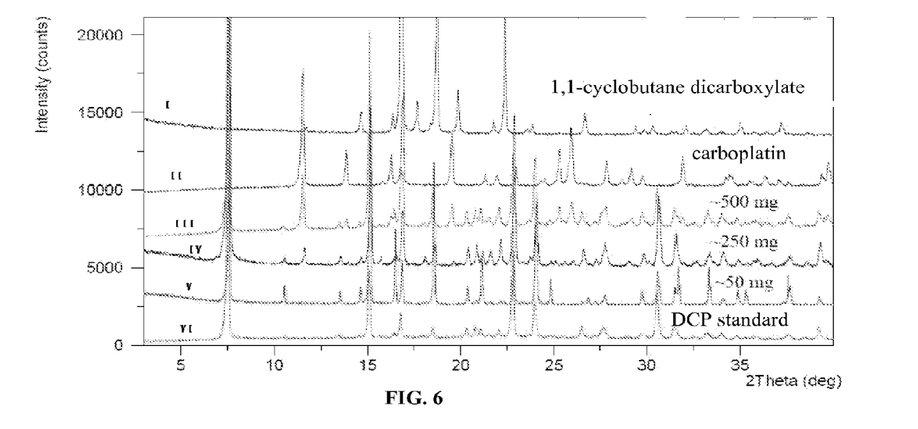
FIG. 6 shows representative XRPD patterns of the product and the patterns are compared to standard dicycloplatin and carboplatin patterns.

The XRPD results are shown in FIG. 6. On scales of or higher than approximately 250 mg, the final product contained not only dicycloplatin, but also a significant amount of carboplatin, demonstrated by the XRPD patterns in FIG. 6, where the product XRPD patterns illustrate similar peaks compared to the standard carboplatin XRPD. Moreover, carboplatin proved difficult to remove, rendering the entire product unusable.

The high level of carboplatin present in the final product may be due to several reasons. Using a 1:1 molar ratio may be one reason that carboplatin are still present.

Since evaporation was required in the reported process, dicycloplatin was degraded in the product because it is sensitive to high temperature.

Moreover, in additional polymorph studies of dicycloplatin, it was recognized that the use of shorter aliphatic alcohols (as reported in U.S. Pat. No. 6,699,901) such as methanol, ethanol, isopropanol and butanol led to a significant amount of carboplatin being left in the product because of disproportionation. In addition, the water solubility of dicycloplatin is limited (40 mg/mL at room temperature), and it was observed that a slurry of dicycloplatin in hot water caused partial hydrolysis). Thus, recrystallization in water was not efficient and was difficult to scale up.

As indicated by the results of the current Examples, the reported process was not robust and was difficult to scale up.

Example 10

Preparation of Dicycloplatin Using Dichloromethane (DCM) as a Solvent

1) Charged 500 mg of carboplatin (1.347 mmol) in 20 mL of DCM in a 50-mL of flask and stirred the suspension to obtain a clear solution at RT.
2) Added 582 mg of 1,1-cyclobutane dicarboxylic acid (4.038 mmol) into the same flask.
3) Stirred the solution in vial wrapped with aluminum-foil at 20~35° C.
4) Stirred over 12 hours and then filtered, washed with DSM.

Figure 7:
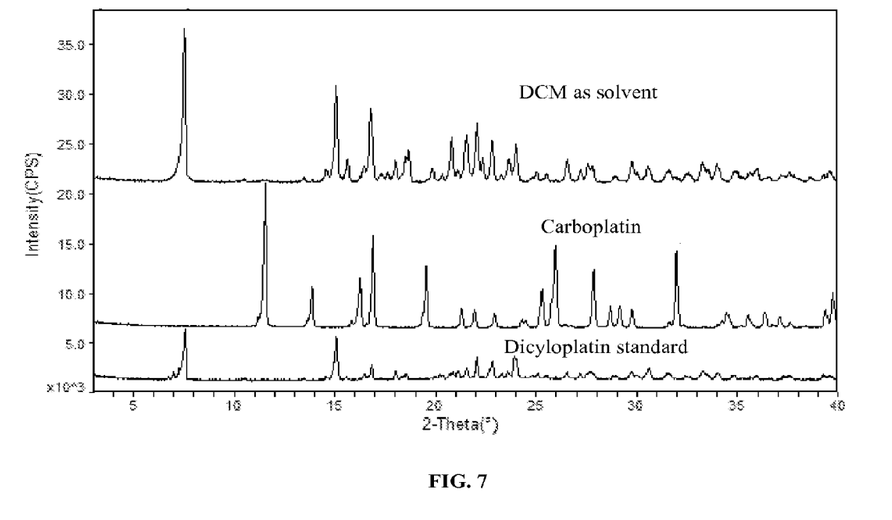
FIG. 7 shows a representative XRPD pattern of the product, where the product contains dicycloplatin and is compared to a standard XRPD pattern of dicycloplatin and carboplatin.

The product obtained by this example was analyzed by XRPD, DSC and TGA. FIG. 7 shows a representative XRPD pattern for the product obtained according to the process of Example 10. The results indicate that the product contained dicycloplatin, with less than traceable amounts of carboplatin.

Example 11

Preparation of Dicycloplatin Using Different Solvents

Different solvents, including organic solvents, were used for the preparation of dicycloplatin. A summary of the products is provided in Table 10.

TABLE 10

| solvent (v/v) | mol ratio (A/B) | | | | | |
|---|---|---|---|---|---|---|
| | 10:1 | 2:1 | 1:1 | 1:2 | 1:5 | 1:10 |
| EtOH/H₂O (19:1) | A | A | A | A + C | | (A + B + C) |
| ACN/H₂O (9:1) | A | A | A | A | | (A + B + C) |
| Acetone/H₂O (19:1) | A | A | A | A | | (B + C)* |
| 1,4-dioxane/H₂O (9:1) | A | A | A | A | | (B + C)* |
| H₂O | | A | A | (A + B + C) | (B + C)* | (B + C)* | (B + C)* |
| DCM | | A | A | A | (A + B + C) | (B + C)* | (B + C)* |
| Isopropanol | A | A | A | A + C | | (A + B + C) |
| Isopropanol/H₂O (3:1) | | | | | | (A + B + C) |
| Toluene | | | | | | (B + C)* |
| THF | | | | | | (A + B + C) |
| Acetone | | | | | | (B + C)* |
| EtOAc | A | A | A | A + B | | (B + C)* |

(1) A: carboplatin; B: 1,1-cyclobutane carboxylic acid; C: dicycloplatin
(2) *indicates that substantially pure dicycloplatin was obtained in a significant quantity after further processing such as filtering, washing and drying.

What is claimed is:

1. A process for preparing dicycloplatin of formula (I), (I)

comprising:
  combining carboplatin with a corresponding proportion of 1,1-cyclobutane dicarboxylic acid and a solvent to form a suspension;
  separating formed precipitated solids from the suspension; and
  drying the solids,
  wherein the solids comprise the dicycloplatin of formula (I) without a detectable amount of carboplatin present, and
  wherein the molar ratio of the carboplatin and the 1,1-cyclobutane dicarboxylic acid in the combining step ranges from about 1:1.15 to 1:50.

2. The process of claim 1, wherein the solids comprise dicycloplatin of formula (I) without any amount of carboplatin detectable by XRPD.

3. The process of claim 1, further comprising cooling the precipitating solids before the separating step.

4. The process of claim 1, further comprising agitating the suspension after the combining step and before the separating step.

5. The process of claim 1, wherein the solids consist essentially of dicycloplatin.

6. The process of claim 1, wherein the solids consist of dicycloplatin.

7. The process of claim 1, wherein the solvent is water.

8. The process of claim 1, wherein the molar ratio of the carboplatin and the 1,1-cyclobutane dicarboxylic acid in the combining step ranges from about 1:15 to about 1:50.

9. The process of claim 1, wherein the molar ratio of the carboplatin and the 1,1-cyclobutane dicarboxylic acid in the combining step ranges from about 1:1.15 to 1:2.

10. The process of claim 1, wherein the proportion of the weight of carboplatin in grams and the volume of the solvent in mL in the combining step ranges from about 1:2 to about 1:50.

11. The process of claim 1, wherein the proportion of the weight of the carboplatin in grams and the volume of the solvent in mL in the combining step ranges from about 1:3 to about 1:5.

12. The process of claim 1, wherein the dicycloplatin has an X-ray powder diffraction pattern substantially as depicted in FIG. 2.

13. The process of claim 1, wherein the reaction temperature of the combining step ranges from 0° C. to 80° C.

14. The process of claim 1, wherein the reaction temperature of the combining step ranges from 10 to 25° C.

15. The process of claim 1, wherein the solvent is an organic solvent selected from the group consisting of: tetrahydrofuran (THF), dichloromethane (DCM), isopropanol, ethanol, ethyl acetate (EtOAc), dimethylformamide (DMF), 1,4-dixoane, acetone, toluene, isobutyl acetate, isopropyl acetate, chloroform, 2-methoxyethanol, methyl isobutyl ketone (MIBK), methyl tert-butyl ether (MTBE), 1,2-dichloro ethane, and a mixture thereof.

16. The process of claim 1, wherein the solvent is a mixture of water and an organic solvent selected from the group consisting of: THF, DCM, isopropanol, ethanol, EtOAc, DMF, 1,4-dixoane, acetone, and a mixture thereof.

17. The process of claim 12, wherein the reaction temperature of the combining step ranges from 0° C. to 80° C.

18. The process of claim 12, wherein the reaction temperature of the combining step ranges from 20 to 35° C.

19. The process of claim 12, wherein the molar ratio of the carboplatin and the 1,1-cyclobutane dicarboxylic acid in the combining step ranges from 1:3 to about 1:50.

20. The process of claim 12, wherein the molar ratio of the carboplatin and the 1,1-cyclobutane dicarboxylic acid in the combining step ranges from 1:5 to 1:10.

* * * * *